United States Patent [19]
Roberts et al.

[11] Patent Number: 5,906,961
[45] Date of Patent: May 25, 1999

[54] ALKANOLAMIDE SPREADER-STICKER SURFACTANT COMBINATION

[75] Inventors: Johnnie R. Roberts, Memphis; Greg Volgas, Bartlett, both of Tenn.

[73] Assignee: Helena Chemical Company, Memphis, Tenn.

[21] Appl. No.: 08/865,091

[22] Filed: May 29, 1997

[51] Int. Cl.[6] .......................... A01N 25/02; A01N 25/30; B01F 17/22; C05G 5/00
[52] U.S. Cl. .................. 504/116; 71/64.1; 71/DIG. 1; 424/405; 424/398; 424/525; 504/206; 504/253; 504/343; 504/347; 514/398; 514/525; 516/69; 516/915
[58] Field of Search .................. 252/357; 71/DIG. 1, 71/64.1; 424/405; 504/116; 516/915, 69

[56] References Cited

U.S. PATENT DOCUMENTS

| | | |
|---|---|---|
| 3,894,149 | 7/1975 | Mast ...................................... 71/DIG. 1 |
| 4,770,694 | 9/1988 | Iwasaki et al. ....................... 71/DIG. 1 |
| 4,997,592 | 3/1991 | Woogerd ............................... 71/DIG. 1 |
| 5,108,661 | 4/1992 | Boiteux et al. ........................... 252/357 |
| 5,178,795 | 1/1993 | Roberts .................................... 252/356 |
| 5,234,919 | 8/1993 | Roberts .................................... 514/119 |
| 5,393,791 | 2/1995 | Roberts .................................... 514/762 |
| 5,435,821 | 7/1995 | Duvdevani et al. ................. 504/116 X |
| 5,543,384 | 8/1996 | Brennan .................................. 504/116 |
| 5,580,567 | 12/1996 | Roberts .................................... 424/405 |
| 5,622,911 | 4/1997 | Hasebe et al. .......................... 504/116 |
| 5,624,883 | 4/1997 | Basu et al. .............................. 504/116 |
| 5,639,711 | 6/1997 | Kassebaum et al. ................ 71/DIG. 1 |
| 5,674,514 | 10/1997 | Hässlin .................................... 424/405 |
| 5,780,390 | 7/1998 | Hintz et al. ............................. 504/116 |

*Primary Examiner*—Richard D. Lovering
*Attorney, Agent, or Firm*—Connolly & Hutz

[57] ABSTRACT

An adjuvant composition containing at least an alkanolamide surfactant and optionally other surfactants or pesticides or formulation aids. The surfactant preferably is reacted with a fatty acid. The process preferably takes places without the use of alkoxylation.

27 Claims, No Drawings

ALKANOLAMIDE SPREADER-STICKER SURFACTANT COMBINATION

BACKGROUND OF THE INVENTION

In order to enhance or modify the chemical and/or physical characteristics of certain pesticides, certain materials are added to form a mixture for spraying. Generally referred to as adjuvants, these materials have no pesticidal activity of their own. Since spray application can be critical to the performance of the agricultural chemical, adjuvants are added to reduce application problems such as chemical stability, incompatibility, solubility, suspension, foaming, drift, evaporation, volatilization, phytotoxicity, surface tension, droplet size and coverage. They can, depending on their type, enhance wetting, spreading, sticking, emulsifying, dispersing and biological activity. Adjuvants include wetting agents, crop oil concentrates, spreaders, stickers, buffering agents, foaming and anti-foaming agents, dispersing agents and drift control agents.

Over 200 EPA-registered pesticides have specific recommendations on their labels for adjuvant use. These are recommended for one of two reasons. The first reason is to enhance biological activity of the pesticide. The second reason would be to reduce, minimize or eliminate spray application problems as noted previously. There are several different types of adjuvants recommended. To achieve consistent, effective results from them, the user must first select the desired type of adjuvant and then the appropriate product within that specific type for use with a particular pesticide and then use that product at recommended rates.

Many pesticide labels require or recommend the use of a "spreader-sticker" with the use of the pesticide. The American Society of Testing and Materials defines spray adjuvant terminology in their document E1519-94a which is incorporated by reference in its entirety. This organization has defined a spreader as "a material which increases the area that a droplet of a given spray mixture will cover on a target." A sticker is defined as "a material that assists the spray deposit to adhere or stick to the target and may be measured in terms of resistance to time, wind, water, mechanical action, or chemical action." A spreader-sticker is defined as "a material that has the properties of both a spreader and a sticker".

Historically, many materials have been used as stickers in pesticide-based spray mixtures. A polymer of Beta-pinene is currently marketed by Helena Chemical Company and by Miller. A latex-based resin has been marketed by United Agri-Products and others. Several resins have been used as sticking agents. Free fatty acids have been also been used as stickers. U.S. Pat. No. 5,543,384 describes a method of making a sticker-extender for pesticides comprising a first mixture containing an anhydride, an acid and turpentine mixed with a second mixture containing an isomeric alcohol and at least one amino alcohol. All of these products are essentially hydrophobic film-formers and require the use of emulsifiers or co-surfactants to disperse them in water for the initial application. The surfactants used for emulsifying or dispersing the stickers are generally what is relied upon for the spreader functionality of these products.

Historically, these products have not provided significant spreading if they do indeed actually enhance sticking, or they do not provide significant sticking if they do indeed actually enhance spreading. It would be advantageous to combine both of these functions effectively into one single product. This would provide ease of use for the consumer.

The beta-pinene based products have historically caused mixing problems with some pesticides. Specifically, dry flowable or wettable powder formulations, can interact with beta-pinene emulsions and cause severe tank mixing problems. Beta-pinene, latex, and free fatty acids can also leave undesirable films in spray tanks which cause clean-out problems for pesticide applicators.

Latex-based stickers have provided excellent sticking capabilities, but have formed water-impermeable films on plant surfaces. This film does not allow contact between pest and pesticide, which is essential for contact pesticides.

U.S. Pat. Nos. 5,178,795; 5,393,791 and 5,580,567 are all issued to Johnnie R. Roberts which are all incorporated herein. These patents describe a homogenous non-aqueous adjuvant composition comprising a spray oil and surfactant blend with an acidic pH of less than about 7. In addition, these patents require an oil or its equivalent. However, contrary to the Roberts' patents, the applicants have found that the novel spreader-sticker surfactant combination works without an oil or its equivalent being required and best in the basic range having a pH of greater than about 7 and preferably at least about 8. The adjuvants described in all three Roberts patents are excluded from this invention and the claimed invention.

Alkanolamide surfactants have not been used frequently in agriculture. These surfactants have been used for a number of years as thickeners in the personal care industry. Alkanolamides have also been widely used as foam stabilizers in the laundry and detergent industry.

U.S. Pat. No. 5,622,911 which is incorporated by reference in its entirety, describes a method for enhancing the efficacy of agricultural chemical with alkoxylated fatty acid amides. The fatty acid acids correspond to $R^1$. The fatty acid amides must be alkoxylated with ethoxy $\{(CH_2R^{2\ or\ 3} CHO)$ having $R^{2\ or\ 3}$ as hydrogen$\}$ or isopropoxy $\{(CH_{2\ or\ 3} CHO)$ having $R^{2\ or\ 3}$ as methyl$\}$. We have found an agricultural product that is not alkoxylated and a method of making an agricultural product without alkoxylation being required.

It is the object of this invention to provide an effective sticker in combination with an effective spreader in a single phase adjuvant composition or in a single phase pesticide composition. These formulations do not leave residues in spray tanks which give applicators clean-out problems. Alkanolamide spreader stickers have not caused any mixing problems with dry pesticide tank mixes.

SUMMARY OF THE INVENTION

The present invention is a homogeneous adjuvant composition containing at least an alkanolamide surfactant and optionally other surfactants or pesticides or formulation aids at a pH of at least 7, preferably at least about 8. Preferably the alkanolamide is a fatty acid that is not ethoxylated or propoxylated or even alkoxylated. When these mixtures are mixed with other pesticide spray mixtures, the composition enhances spreading of the applied droplets, and reduces the tendency for the dried deposit to be washed off of plant surfaces by rain or heavy dews.

DETAILED DESCRIPTION OF THE INVENTION

This invention is a homogeneous blend of alkanolamide surfactants and optionally other surfactants having the ability to enhance spreading of agrochemical sprays and reduce the tendency for the dried deposit to be washed off by environmental factors. The adjuvant preferably does not not contain a spray oil mixed with a buffering agent or a spray oil without a buffering provided that the pH of the adjuvant is less than 7. The adjuvants of all three Roberts patents are explicitly excluded. The pH of the adjuvant could be acidic or basic. It is possible to have a pH of at least 7 and preferably at least 8. Preferably the alkanolamide is a fatty acid that is not ethoxylated or propoxylated or even alkoxylated. The alkanolamides employed in this invention include, but are not limited to those derived from fatty acids and their esters reacted with an alkanolamine. The fatty acids and their esters can be reacted with an alkanolamine and mixed with an alkylated vegetable oil or an alkylated fatty acid and the adjuvant has a pH of at least 7. The alkanolamides have the general structure of:

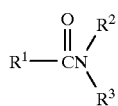

where $R^1$ is a $C_4$–$C_{40}$ hydrocarbon such as but not limited to a fatty alkyl group or alkenyl group, $R^2$ and $R^3$ are identical or different and are either hydrogen, $C_xH_{2x}OH$ where x equals 1–40.

The alkanolamide can be co-formulated with any spreader as defined by ASTM. The preferred surfactants are:

a) sorbitan fatty acids and sorbitan fatty acid esters and their ethoxylated or propoxylated derivatives, b) silicone surfactants of the formula

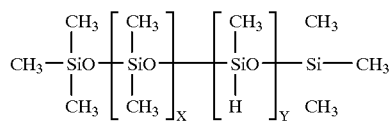

where X is 1 to 100 and Y equals 1 to 100, c) silicone surfactants of the formula

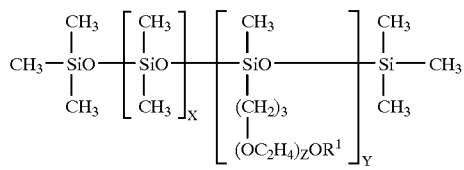

where X is 1 to 100 and Y is 1 to 100 and Z is 1 to 100 and $R^1$ is an alkyl preferably containing from one to 40 carbon atoms and most preferably ethyl or propyl group, d) ethoxylated fatty acids, e) branched and linear alkyl ethoxylates and phosphate or carboxylate acid esters thereof, f) alkylphenol ethoxylates and phosphate or carboxylate acid esters thereof, g) polypropylene and polyethylene glycols, and h) block copolymers of ethylene oxide and propylene oxide and phosphate or carboxylate acid esters thereof.

Optionally, the alkanolamide or alkanolamide and surfactant mixture can be mixed with any agrochemical to provide spreading and sticking properties to the final agrochemical spray solution.

The invention further relates to an agricultural spray adjuvant consisting essentially of alkanolamide surfactants and a pesticide wherein said adjuvant has pH of at least 7 and preferably greater than 8. The pesticide can be an insecticide such as, but not limited to acephate, malthion, dimethoate, mineral oil or carbaryl. The pesticide could also be a herbicide such as, but not limited to glyphosate, trifluralin, sethoxydim, imazethapyr or a phenoxy based herbicide such as 2, 4-D. The pesticide can be a fungicide such as, but not limited to copper-based, chlorothalonil and isoiprodione. Furthermore, the spray adjuvant can contain a nutritional such as, but not limited to a fertilizer, a micronutrient.

The following examples are used to illustrate the invention, but are not to be used as limit the invention.

EXAMPLES

Example 1

A series of alkanolamides were tested for their sticking ability against a commercially available spreader sticker known as Nufilm P, sold by Miller Chemical. The alkanolamides were used at 0.5% (v/v) against Nufilm P at 0.1% (v/v) in a spray mixture containing Atrazine 90 DF. Atrazine 90 DF is a commercially available herbicide containing 90% of the active ingredient atrazine and 10% inerts. The solutions were prepared and droplets of each solution were placed on glass watch glass plates to a weight of 3.0 grams. These plates were allowed to dry and then subjected to simulated rainfall. The residues of atrazine were then extracted from the plates and analyzed using gas-liquid chromatography in conjunction with a flame ionization detector. The results are reported below as the percentage of the applied pesticide that remained on the glass plates after simulated rainfall.

| Treatment | % Atrazine remaining |
|---|---|
| Control (Atrazine 90 DF alone in water) | None detected |
| Nufilm P (0.1% with Atrazine 90 DF in water) | 2.3% |
| Ninol LMP (0.5% with Atrazine 90 DF in water) | 20.3% |
| Ninol 96-SL (0.5% with Atrazine 90 DF in water) | 36.7% |

Ninol LMP is a lauryl acid alkanolamide derived from monoethanolamine. Ninol 96-SL is a lauryl acid alkanolamide derived from diethanolamine.

This test clearly shows the ability of alkanolamides to provide sticking properties even better than conventional and commercial spreader-stickers.

Example 2

Again, a series of alkanolamides were tested for their sticking ability against a commercially available spreader sticker known as Nufilm P, sold by Miller Chemical. This time, an organosilicone surfactant known commercially as Silwet L-77 was added to the alkanolamide spray mixtures. The alkanolamides were used at 1.9% (v/v) plus 0.1% (v/v) of Silwet L-77 (to provide spreading characteristics) against Nufilm P at 0.5% (v/v) (with and without 0.1% Silwet L-77) in a spray mixture containing Atrazine 90 DF. Also, alkanolamides were tested at 2.0% v/v with Atrazine 90 DF and no additional surfactant added. Atrazine 90 DF is a commercially available herbicide containing 90% of the active ingredient atrazine and 10% inerts. The solutions were prepared and droplets of each solution were placed on glass watch glass plates to a weight of 3.0 grams. These plates were allowed to dry and then subjected to simulated rainfall. The residues of atrazine were then visually ranked from 0–10, with 10 being the best, based on the amount of Atrazine remaining on the glass plate. The results are reported below as an average of two observations and visual rankings.

| Treatment | Visual Ranking (0–10) |
|---|---|
| Control (Atrazine 90 DF alone in water) | 0 |
| Nufilm P (0.5% with Atrazine 90 DF in water) | 5.5 |
| Nufilm P (0.5% with Atrazine 90 DF in water) plus 0.1% Silwet L-77 | 0 |
| Ninol 90201 (2.0% with Atrazine 90 DF in water) | 7.5 |
| Ninol 90201 (1.9% with Atrazine 90 DF in water) plus 0.1% Silwet L-77 | 8 |
| Ninol 40-CO (2.0% with Atrazine 90 DF in water) | 6.5 |
| Ninol 40-CO (1.9% with Atrazine 90 DF in water) plus 0.1% Silwet L-77 | 6.5 |

Ninol 40-CO is a coca fatty acid alkanolamide derived from diethanolamine. Ninol 90201 is a oleic acid alkanolamide derived from diethanolamine.

This test clearly shows that alkanolamides provide sticking properties comparable or better than commercial spreader stickers. Furthermore, this test demonstrates the effect of additional and meaningful spreading characteristics added to the spray mixture. The commercial spreader-sticker Nufilm P loses all of it's sticking ability when Silwet L-77 is added. The alkanolamides have not lost sticking abilities when the Silwet L-77 was added.

While there is shown and described herein certain specific structures embodying the invention, it will be manifest to those skilled in the art that various modifications and rearrangements of the parts may be made without departing from the spirit and scope of the underlying inventive concept and that the same is not limited to the particular forms herein shown and described.

We claim:

1. An agricultural spray adjuvant consisting essentially of a non-ethoxylated or propoxylated alkanolamide surfactant of the formula where $R^1$ is a $C_1$–$C_{40}$ hydrocarbon, $R^2$ is hydrogen or $C_xH_{2x}OH$ where x equals 1–40 and $R^3$ is $C_{x'}H_{2x'}OH$ where x' equals 1 or 4–40 with the proviso that (a) said adjuvant does not contain a spray oil mixed with a buffering agent that reduces the pH of said adjuvant to 7 or less or (b) said adjuvant does not contain a spray oil mixed without a bufferng agent provided that the pH of said adjuvant is 7 or less.

2. The agricultural spray adjuvant as claimed in claim 1, which optionally contains additional surfactants, wherein the spray adjuvant has a surface tension of less than 60 dynes as measured by the Du Nuoy Surface Tensiometer at a concentration of 0–10%.

3. The agricultural spray adjuvant as claimed in claim 1, further containing at least one surfactant selected from the group consisting of:

a) sorbitan fatty acids and sorbitan fatty acid esters and their ethoxylated, or propoxylated derivatives, b) silicone surfactants of the formula 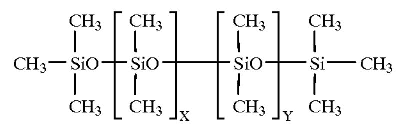 where X equals 1 to 100 and Y equals 1 to 100, c) silicone surfactants of the formula 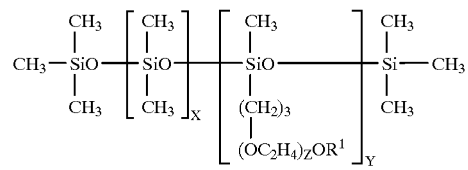 where X, Y and Z and independently of one another are from 1 to 100 and $R^1$ is a $C_1$–$C_{40}$ alkyl, d) ethoxylated fatty acids, e) branched and linear alkyl ethoxylates and phosphate or carboxylate acid esters thereof, f) alkylphenol ethoxylates and phosphate or carboxylate acid esters thereof, g) polypropylene and polyethylene glycols, and h) block copolymers of ethylene oxide and propylene oxide and phosphate or carboxylate acid esters thereof.

4. The agricultural spray adjuvant as claimed in claim 1, further containing at least one pesticide.

5. The agricultural spray adjuvant as claimed in claim 4, wherein said at least one pesticide is at least one insecticide.

6. The agricultural spray adjuvant as claimed in claim 5, wherein at least one insecticide is selected from the group consisting of acephate, malathion, dimethoate, mineral oil and carbaryl.

7. The agricultural spray adjuvant as claimed in claim 4, wherein said at least one pesticide is at least one herbicide.

8. The agricultural spray adjuvant as claimed in claim 7, where said herbicide is at least one selected from the group consisting of glyphosate, trifluralin, sethoxydim, imazethapyr and phenoxy based herbicide.

9. The agricultural spray adjuvant as claimed in claim 4, wherein at least one pesticide is at least one fungicide.

10. The agricultural spray adjuvant as claimed in claim 8, where said fungicide is copper-based, chlorothalonil or iprodione.

11. The agricultural spray adjuvant as claimed in claim 1, which further contains a nutritional.

12. The agricultural spray adjuvant as claimed in claim 11, wherein said nutritional is a fertilizer.

13. The agricultural spray adjuvant as claimed in claim 11, wherein said nutritional is a micronutrient.

14. The agricultural spray adjuvant as claimed in claim 1, which further contains a mineral oil.

15. The agricultural spray adjuvant as claimed in claim 1, further containing a vegetable oil.

16. The agricultural spray adjuvant as claimed in claim 1, wherein x is 1, 3, 4 or 5.

17. The agricultural spray adjuvant as claimed in claim 1, wherein x is 1, 4 or 5.

18. The agricultural spray adjuvant as claimed in claim 1, further containing an alkylated vegetable oil or alkylated fatty acid.

19. The agricultural spray adjuvant as claimed in claim 1, wherein the pH is at least 7.

20. The agricultural spray adjuvant as claimed in claim 1, wherein the pH is at least 8.

21. A process to make an agricultural spray adjuvant consisting essentially of mixing at least one fatty acid or its ester with a compound of the formula

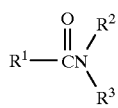

where
$R^1$ is a $C_1$–$C_{40}$ hydrocarbon,
$R^2$ is hydrogen or $C_xH_{2x}OH$ where x equals 1–40 and
$R^3$ is $C_{x'}H_{2x'}OH$ where x' equals 1 or 4–40,
to produce the spray adjuvant which has a pH of at least 7.

22. The process as claimed in claim 20, wherein the pH is at least 8.

23. The process as claimed in claim 20, wherein the process takes place without the use of alkoxylation.

24. An agricultural spray adjuvant produced by the process as claimed in claim 20.

25. A process to make an agricultural spray adjuvant consisting essentially of mixing at least one fatty acid or its esters with a compound

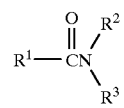

where
$R^1$ is a $C_1$–$C_{40}$ hydrocarbon,
$R^2$ is hydrogen or $C_xH_{2x}OH$ where x equals 1–40 and
$R^3$ is $C_{x'}H_{2x'}OH$ where x' equals 1 or 4–40,
to produce the spray adjuvant with the proviso that
  (a) said adjuvant does not contain a spray oil mixed with a buffering agent that reduces the pH of said adjuvant to 7 or less or
  (b) said adjuvant does not contain a spray oil mixed without a buffering agent provided that the pH of said adjuvant is 7 or less.

26. The process as claimed in claim 25, wherein the process takes place without the use of alkoxylation.

27. An agricultural spray adjuvant consisting essentially of a non-ethoxylated or propoxylated alkanolamide surfactant of the formula

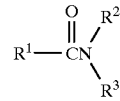

where
$R^1$ is a $C_1$–$C_{40}$ hydrocarbon,
$R^2$ and $R^3$ independently of one another are $C_xH_{2x}OH$ where x equals 1 or 4–40 and with the proviso that
  (a) said adjuvant does not contain a spray oil mixed with a buffering agent that reduces the pH of said adjuvant to 7 or less or
  (b) said adjuvant does not contain a spray oil mixed without a buffering agent provided that the pH of said adjuvant is 7 or less.

* * * * *